United States Patent
Osborn et al.

(10) Patent No.: US 10,134,496 B2
(45) Date of Patent: Nov. 20, 2018

(54) METHODS AND SYSTEMS FOR EMPTYING A WASTE VESSEL

(71) Applicant: GE Healthcare Limited, Buckinghamshire (GB)

(72) Inventors: Nigel John Osborn, Amersham (GB); Julian Grigg, Amersham (GB); Eric Horn, Auckland (NZ); Jonathan Robert Shales, Amersham (GB)

(73) Assignee: GE Healthcare Limited Company, Little Chalfont, Buckinghamshire (GB)

( * ) Notice: Subject to any disclaimer, the term of this patent is extended or adjusted under 35 U.S.C. 154(b) by 46 days.

(21) Appl. No.: 15/104,373

(22) PCT Filed: Dec. 19, 2014

(86) PCT No.: PCT/EP2014/078807
§ 371 (c)(1),
(2) Date: Jun. 14, 2016

(87) PCT Pub. No.: WO2015/091985
PCT Pub. Date: Jun. 25, 2015

(65) Prior Publication Data
US 2016/0314866 A1    Oct. 27, 2016

Related U.S. Application Data

(60) Provisional application No. 61/918,971, filed on Dec. 20, 2013.

(51) Int. Cl.
G21F 9/22    (2006.01)
G21F 9/06    (2006.01)
(Continued)

(52) U.S. Cl.
CPC ............... *G21F 9/22* (2013.01); *A61K 51/00* (2013.01); *B65B 3/003* (2013.01); *B67D 7/0294* (2013.01);
(Continued)

(58) Field of Classification Search
CPC ..... G21F 9/06; G21F 9/20; G21F 9/22; B67D 7/02; B67D 7/0288; B67D 7/0294; B65B 3/003; A61J 3/002; A61K 51/00
See application file for complete search history.

(56) References Cited

U.S. PATENT DOCUMENTS 6,893,425 B2 *   5/2005   Dunn .................... A61L 11/00
                                                    604/319
7,621,898 B2 *  11/2009   Lalomia ............... F24F 3/1603
                                                    119/14.46
(Continued)

FOREIGN PATENT DOCUMENTS

DE          2526424 A1     12/1976
WO       2012/092564 A2     7/2012
WO    WO 2012157898 A2 *   11/2012    ............. C07B 59/00

OTHER PUBLICATIONS

International Search Report and Written Opinion regarding International Application No. PCT/EP2014/078807, dated May 12, 2015, 9 pages.

*Primary Examiner* — Nicolas A Arnett

(57) ABSTRACT

Methods and devices for directing a waste fluid from a radiopharmaceutical synthesis system to a waste vessel are provided. In one example, the method includes serially connecting a primary waste vessel to a secondary waste vessel with a fluid conduit, including a waste valve connected to the fluid conduit extending between the primary waste vessel and secondary waste vessel; opening the waste valve so as to allow fluid communication between cavities of the primary and secondary waste vessels; drawing a low
(Continued)

pressure in both waste vessels; closing the waste valve so as to fluidically isolate the secondary waste vessel from the primary waste vessel, discharging the waste fluid through a pump valve into the primary waste vessel, and opening the waste valve to evacuate the waste fluid from the primary waste vessel into the secondary waste vessel.

16 Claims, 3 Drawing Sheets

(51) Int. Cl.
*G21F 9/20* (2006.01)
*A61K 51/00* (2006.01)
*B65B 3/00* (2006.01)
*B67D 7/02* (2010.01)
*A61J 3/00* (2006.01)

(52) U.S. Cl.
CPC ............. *G21F 9/06* (2013.01); *G21F 9/20* (2013.01); *A61J 3/002* (2013.01)

(56) References Cited

U.S. PATENT DOCUMENTS

| | | | |
|---|---|---|---|
| 7,879,228 B2* | 2/2011 | Dunn | A61L 11/00 137/205 |
| RE44,920 E * | 6/2014 | Dunn | A61L 2/18 210/143 |
| 8,740,866 B2* | 6/2014 | Reasoner | A61M 1/0005 119/14.46 |
| 9,770,541 B2* | 9/2017 | Carr | A61M 1/0007 |
| 2003/0164600 A1* | 9/2003 | Dunn | A61L 11/00 280/47.34 |
| 2007/0135779 A1* | 6/2007 | Lalomia | A61M 1/0005 604/319 |
| 2010/0049152 A1* | 2/2010 | Lalomia | A61M 1/0005 604/319 |
| 2012/0048424 A1* | 3/2012 | Giribona | B65B 3/003 141/311 R |
| 2013/0269825 A1* | 10/2013 | Osborn | A61J 1/2089 141/1 |
| 2014/0213757 A1* | 7/2014 | Shales | G21H 5/02 530/317 |
| 2015/0086476 A1* | 3/2015 | Eriksson | C07B 59/00 424/1.11 |

* cited by examiner

METHODS AND SYSTEMS FOR EMPTYING A WASTE VESSEL

CROSS-REFERENCE TO RELATED APPLICATIONS

This application is a filing under 35 U.S.C. 371 of international application number PCT/EP2014/078807, filed Dec. 19, 2014, which claims priority to U.S. application No. 61/918,971, filed Dec. 20, 2013, the entire disclosures of each of which are hereby incorporated by reference.

FIELD OF THE INVENTION

The present invention relates to the production of radiopharmaceuticals. More particularly, the present invention is directed to a system and method for automatically emptying a primary waste vessel containing radioactive waste fluid.

BACKGROUND OF THE INVENTION

In the field of radiopharmaceutical synthesis, automated synthesizers are employed to operate within the confines of a hot cell to perform the steps of synthesizing and dispensing a radiopharmaceutical. Space within a hot cell is generally at a premium as for each synthesizer a hot cell must as well accommodate ancillary equipment to the synthesizer, such as an HPLC injector and column, dispense vials, waste vessels, reagent vessels, and connective tubing associated with each synthesizer. Between synthesis runs on a synthesizer, an operator typically needs access to the hot cell to, eg, swap out synthesis cassettes used with the synthesizer, check connections to or from the synthesizer or cassette, etc. The waste vessel associated with the synthesis run can contain a significant proportion of the activity that originally came from the cyclotron, as much as 60% of that starting activity. When the operator must empty the waste container between runs, wait times will be increased for radioisotopes having a longer half-life, e.g., 18-F which has a 2-hour half-life. Thus, the waste vessels provided within the hot cell may contain a source of significant radioactive hazard to the operator. While the waste vessel may be shielded, such shielding takes up additional space within the hot cell. Additionally, it is almost always specified that the waste vessel be emptied at the beginning of each run for a drug product, because the impact of the presence of the waste on the subsequent run cannot be determined with complete certainty. Thus a subsequent synthesis run can experience a catastrophic failure due to the presence of the waste from a previous run remaining in the waste vessel for the subsequent run.

Systems have been developed for drawing the contents of the waste vessel into a secondary waste vessel, possibly even outside the hot cell in a shielded enclosure, to reduce operator exposure to the activity of the waste fluid. Some previous attempts to provide systems for emptying a waste vessel containing radioactive waste fluid include providing a positive pressure to a container through an inlet port so as to direct the fluid through and outlet port. Systems providing a positive motive pressure to a radioactive fluid run risks of over-stressing the fittings and junctures along the path of fluid flow. Additionally, some synthesis systems may actively limit the pressure that may be imposed on a waste vessel by countering the pumping of additional pressuring gas by applying a vacuum to the waste vessel should the pressure within the waste vessel exceed a pre-set limit.

Other attempts have provided a negative pressure (ie, a low pressure) at the outlet port so as to draw the fluid through the outlet port. See, eg, commonly-assigned WO 2012/092564. These systems providing negative pressure to the waste vessel have provided an active pump for applying the negative pressure through a secondary waste vessel to the primary waste vessel as the motive force for the fluid transfer, thus requiring careful control of the negative pressure pump so as not to overdraw the waste fluid beyond the secondary waste vessel.

The art thus lacks a system and method for utilizing a negative pressure motive force without the need for an active negative pressure pump during the fluid transfer.

SUMMARY OF THE INVENTION

The present invention provides a system and method for automatically emptying the contents of a primary waste vessel into a secondary waste vessel. The present invention provides a secondary waste vessel connected through a waste valve to a primary waste vessel and a vacuum source connected to the primary vessel opposite the secondary vessel. The vacuum source is able to draw down the pressure within the secondary vessel when the waste valve is opened such that closing of the valve will fluidically isolate the secondary vessel from the first vessel and thus also provide a smaller waste vessel volume exposed during synthesis operations. A waste fluid may be directed into the primary waste vessel during a production run and thereafter, the waste valve may be opened so as to produce a pressure differential acting across the waste fluid sufficient to discharge the waste fluid from the primary waste vessel into the low-pressure secondary waste vessel. The primary waste vessel will then be emptied sufficiently to allow a second production run. Desirably, both vessels are only evacuated after the drug product has been dispensed. This latter is much easier to accept from a GMP perspective since the drug product cannot then be impacted by a sequence that is only executed after the drug product has been dispensed.

In order to be able to conduct multiple back-to-back radiosyntheses using an automated synthesis device within a hot cell, it is may be necessary or desirable to empty the contents of the associated waste vessel between runs. A method for preparing a secondary waste vessel is proposed that connects the secondary waste vessel in series with the primary waste vessel. A vacuum can be applied to both vessels, desirably from the synthesis device and through the primary waste vessel, then a waste valve in-between the two vessels may be closed.

Another method of the present invention performs the method for preparing a secondary waste vessel and then directs a waste fluid into the primary waste vessel. Once dispensing into the primary waste vessel is complete, the waste valve may be opened so as to allow the waste fluid to be drawn into the secondary vessel without any user intervention. It is further contemplated that pressure may be applied to the primary waste vessel so as to further assist in directing the waste fluid from the primary waste vessel to the secondary waste vessel. It is further contemplated that the secondary waste vessel may be larger than the primary waste vessel so as to allow multiple evacuations from the primary waste vessel between emptying of the secondary waste vessel.

The methods and devices of the present invention may thus allow for lower mean time between production runs on a synthesis device. Operator exposure to the radioactive contents in the waste vessel is also minimized by first directing those contents into a secondary waste vessel which may be located further away from the operator and in additional protective shielding. This can be especially important when working with radioisotopes having a longer half-life, e.g., 18-F which has a 2-hour half-life, as the activity remaining in the waste vessel within the hot cell would require the operator to wait longer for the activity decay to reach an acceptable level before starting a subsequent production run.

DETAILED DESCRIPTION OF THE PREFERRED EMBODIMENTS

Figure 1:
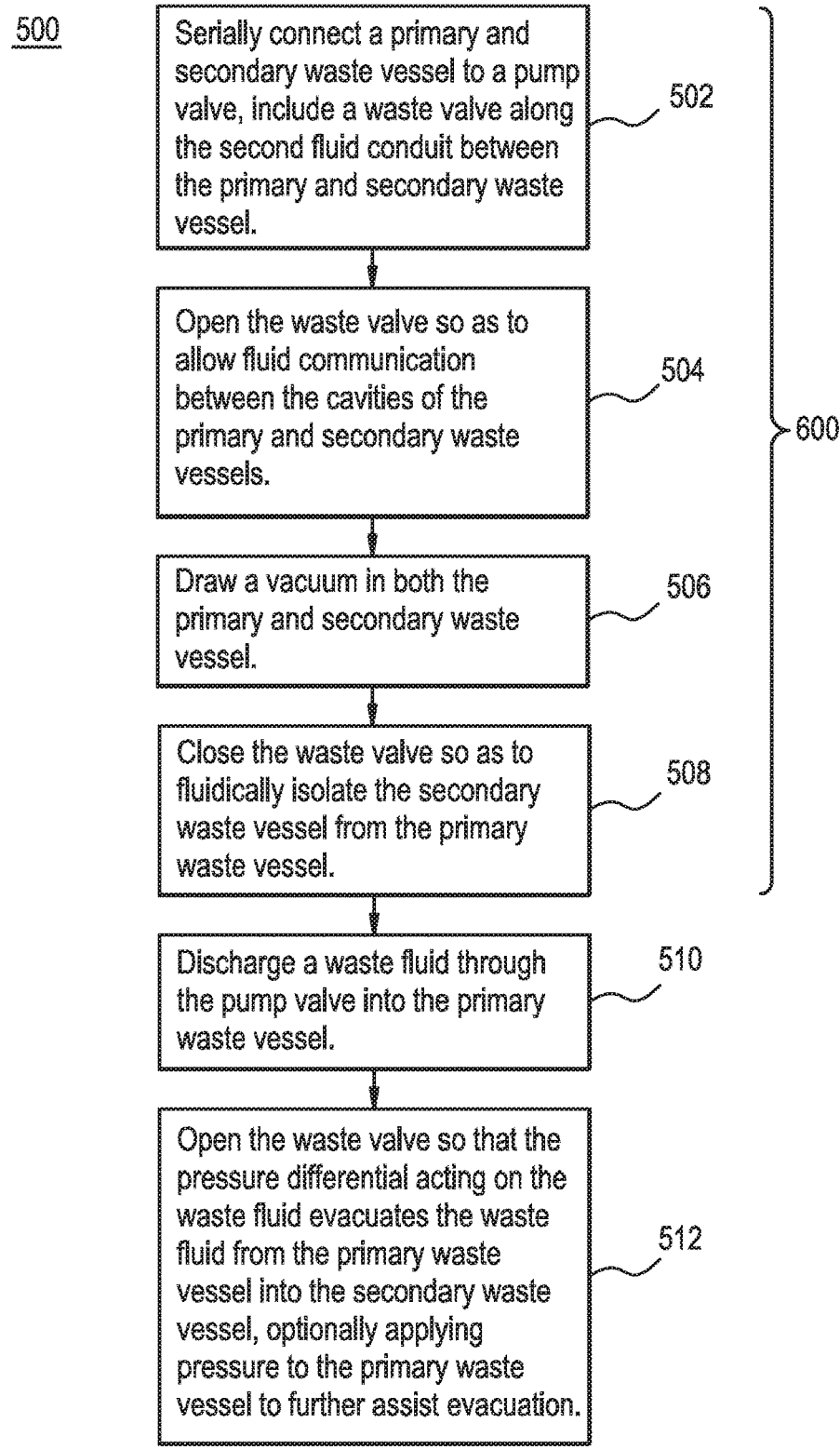
FIG. 1 depicts a flowchart of a method of the present invention, which incorporates another method of the present invention.

Clinical PET centres may have a requirement to perform multiple back-to-back radiosyntheses to allow the production of multiple tracers within their daily production schedule. For some PET centers employing a FASTlab® synthesizer, a hot cell includes the synthesizer connected to a primary waste vessel having a maximum capacity of 250 ml, whereas the total volume of reagents available during a radiosynthesis is typically around 110 ml (100 ml from water bag plus the contents of reagent vials), although it could be even more when able to connect bulk solvents at free positions on a cassette (some of these could end up in the waste vessel). Radiotracers presently in development will likely add external bulk vials to free valves on this synthesizer and thus the waste may add up to significantly above this value. For instance, for a radiotracer synthesis run that produces 130 ml of waste, it would not be possible to perform back-to-back production runs of the same radiotracer first without emptying the waste vessel between those runs. As space within the hot cell is at a premium, it may not be possible to just position a larger waste vessel within the hot cell, so it is thus desirable that the primary waste vessel be emptied between syntheses. Additionally, even if there were a larger waste vessel, regulatory requirements or even the chemical purity results pertaining to the same or different radiotracers may demand that the primary waste vessel be emptied between synthesis runs. By transferring the contents to a secondary waste vessel, which is desirably behind still more shielding, operator exposure to residual activity in the primary waste vessel may be reduced while the operator swaps a new cassette for the spent cassette and also allow for validation of each synthesis run.

The radiopharmaceutical synthesis device of the present invention is preferably an 'automated synthesizer' as described below. More preferably, the automated synthesizer comprises an interchangeable 'cassette' as defined below.

By the term "automated synthesizer" is meant an automated module based on the principle of unit operations as described by Satyamurthy et al [Clin. Positr. Imag., 2(5), 233-253 (1999)]. The term 'unit operations' means that complex processes are reduced to a series of simple operations or reactions, which can be applied to a range of materials. Such automated synthesizers are preferred for the method of the present invention especially when a radiopharmaceutical composition is desired. They are commercially available from a range of suppliers [Satyamurthy et al, above], including: GE Healthcare; CTI Inc; Ion Beam Applications S.A. (Chemin du Cyclotron 3, B-1348 Louvain-La-Neuve, Belgium); Raytest (Germany) and Bioscan (USA).

Commercial automated synthesizers also provide suitable containers for the liquid radioactive waste generated as a result of the radiopharmaceutical preparation. Automated synthesizers are not typically provided with significant radiation shielding for an operator, since they are designed to be employed in a suitably configured radioactive work cell, also known as and previously described as a "hot cell". The radioactive work cell provides suitable radiation shielding to protect the operator from potential radiation dose, as well as ventilation to remove chemical and/or radioactive vapours. The automated synthesizer preferably utilizes a cassette.

By the term "cassette" is meant a unit apparatus designed such that the whole unit fits removably and interchangeably onto an automated synthesizer apparatus (as defined above), in such a way that mechanical movement of moving parts of the synthesizer controls the operation of the cassette from outside the cassette, i.e. externally. Suitable cassettes comprise an array of valves, each linked to a port where reagents or vials can be attached, by either needle puncture of an inverted septum-sealed vial, or by gas-tight, marrying joints. Each valve has a mating joint which interfaces with a corresponding moving arm of the automated synthesizer. External rotation of the arm thus controls the orientation of the valve when the cassette is attached to the automated synthesizer. Additional moving parts of the automated synthesizer are designed to clip onto syringe plunger tips, and thus raise or depress syringe barrels.

The cassette is versatile, typically having several positions where reagents can be attached, and several suitable for attachment of syringe vials of reagents or chromatography cartridges (e.g. solid-phase extraction or SPE). The cassette always comprises at least one reaction vessel. Such reaction vessels are preferably 1 to 10 $cm^3$, most preferably 2 to 5 $cm^3$ in volume and are configured such that 3 or more ports of the cassette are connected thereto, to permit transfer of reagents or solvents from various ports on the cassette. Preferably the cassette has 15 to 40 valves in a linear array, most preferably 20 to 30, with 25 being especially preferred. The valves of the cassette are preferably each identical, and most preferably are 3-way valves. The cassettes are designed to be suitable for radiopharmaceutical manufacture and are therefore manufactured from materials which are of pharmaceutical grade and ideally also are resistant to radiolysis.

Preferred automated synthesizers of the present invention comprise a disposable or single use cassette which comprises all the reagents, reaction vessels and apparatus necessary to carry out the preparation of a given batch of radiofluorinated radiopharmaceutical. Varying configurations and load-outs of different cassettes mean that the automated synthesizer has the flexibility to be capable of making a variety of different radiopharmaceuticals with minimal risk of cross-contamination, by simply changing the cassette. The cassette approach also has the advantages of: simplified set-up hence reduced risk of operator error; improved Good Manufacturing Practice (GMP) compliance; multi-tracer capability; rapid change between production runs; pre-run automated diagnostic checking of the cassette and reagents; automated barcode cross-check of chemical reagents vs the synthesis to be carried out; and reagent traceability.

The term "radiopharmaceutical" has its conventional meaning, and refers to an imaging agent wherein the imaging moiety is a radioisotope. The radiopharmaceutical is labeled with a radioisotope suitable for medical imaging in vivo. By the term "imaging agent" is meant a compound suitable for imaging the mammalian body. Such imaging agents are designed to have minimal pharmacological effect on the mammalian subject to be imaged. Preferably, the imaging agent can be administered to the mammalian body in a minimally invasive manner, i.e. without a substantial health risk to the mammalian subject when carried out under professional medical expertise. Such minimally invasive administration is preferably intravenous administration into a peripheral vein of said subject, without the need for local or general anaesthetic.

The radioisotope of the radiopharmaceutical is preferably suitable for either PET or SPECT imaging in vivo. PET imaging radiopharmaceuticals are often also termed 'radiotracers'. The radioisotope can be metallic (i.e. a radiometal), or a non-metal. When the imaging moiety is a radiometal, suitable radiometals can be either positron emitters such as $^{64}$Cu, $^{48}$V, $^{52}$Fe, $^{55}$Co, $^{89}$Zr, $^{94m}$Tc or $^{68}$Ga; γ-emitters such as $^{99m}$Tc, $^{111}$In, $^{113m}$In, or $^{67}$Ga. Preferred radiometals are $^{99m}$Tc, $^{64}$Cu, $^{68}$Ga, $^{89}$Zr, and $^{111}$In. Most preferred radiometals are γ-emitters, especially $^{99m}$Tc.

When the imaging moiety is a non-metal, it can be a gamma-emitter or a positron emitter. Gamma-emitting radiohalogens are suitably chosen from $^{123}$I, $^{131}$I or $^{77}$Br. A preferred gamma-emitting radioactive halogen is $^{123}$I. When the imaging moiety is a positron-emitting radioactive non-metal, suitable such positron emitters include: $^{11}$C, $^{13}$N, $^{15}$O, $^{17}$F, $^{18}$F, $^{75}$Br, $^{76}$Br or $^{124}$I. Preferred positron-emitting radioactive non-metals are $^{11}$C, $^{13}$N, $^{18}$F and $^{124}$I, especially $^{11}$C and $^{18}$F, most especially $^{18}$F.

Referring to FIG. 1, the present invention provides a method for emptying the contents of a waste vessel that does not risk overpressure of the waste vessel. Using a system of the present invention as described hereinbelow, the method 500 of the present invention includes the step 502 of serially connecting a primary waste vessel to a secondary waste vessel, including a waste valve connected to the fluid conduit extending between the primary waste vessel and secondary waste vessel. The next step 504 is opening the waste valve so as to allow fluid communication between the cavities of the primary and secondary waste valves. The method then provides the step 506 of drawing a low pressure in both waste vessels. Step 506 desirably includes the step of drawing a vacuum using an evacuation pump connected through a pump valve to the primary waste vessel and pulling down to a low pressure in each waste vessel, such pressure being e.g., about 900 mbar, although other low pressures may also be acceptable which place less strain on the evacuation pump. The method then includes a step 508 of closing the waste valve so as to fluidically isolate the secondary waste vessel from the primary waste vessel. The method then includes a step 510 of dispensing a waste fluid through the pump valve into the primary waste vessel, desirably during a production run by a synthesis device, while the secondary waste vessel is fluidically isolated from the primary waste vessel. The method then includes the step 512 of opening the waste valve and desirably (or as stated in FIG. 1, optionally) applying pressure to the primary waste vessel to expose the waste fluid to a pressure differential causing it to discharge into the secondary waste vessel. The present invention contemplates that a pressure differential of at least about 0.5 atm provides sufficient impetus to the discharge. The present invention contemplates the pressure is applied to the primary waste vessel by a pump on-board the synthesizer or cassette or by a source of nitrogen connected to the synthesizer. While a pump may provide about 0.5 to 1.0 atm or more, the source of nitrogen is contemplated to provide about 1 atm to the primary waste vessel. The waste valve is then closed off and a waste fluid is directed into the primary waste vessel. Method 500 may thus transfer waste fluid from the primary waste vessel into the secondary waste vessel with no opportunity for any back flow to occur. Since the pressure in the system never goes above atmospheric, there should be no need to trip a vacuum pump into operation during the fluid transfer due to excessive pressure. It may be desirable during this procedure to switch the pump valve to an unlocked, or open, position in order to keep the primary waste vessel at or below atmospheric pressure and increase the pressure difference with the secondary waste vessel. Additionally, the tubing, or fluid path, in the primary waste vessel that connects to the secondary waste vessel desirably extends to near the bottom, or lowest interior surface, of the vessel so as to maximize the ability to empty the contents from the primary waste vessel. Similarly, the tubing, or fluid path, extending to the secondary waste vessel should not extend too far down into the secondary waste vessel to minimize the risk of back syphoning from the secondary waste vessel while drawing low pressure in the secondary waste vessel while it contains fluid from a previous synthesis run.

The present invention contemplates that both the primary and secondary waste vessels are only evacuated after the drug product has been dispensed, that is, after primary waste vessel has received the waste fluid from a synthesis run. Waiting to draw the low pressure in the secondary waste vessel is more desirably from a GMP perspective since the drug product will already have been dispensed and thus will not be impacted by a sequence that is only executed after the drug product has been dispensed. In this embodiment of the present invention, the waste fluid is delivered to the primary waste vessel so as to submerge the free end of a discharge conduit while not reaching as high as the free end of a fill cannula (or a delivery port defined by the primary waste vessel) through which both the waste fluid is delivered and the low pressure is drawn on the primary waste vessel. The free end of the fill cannula to the primary waste vessel will terminate at a level above the free end of the discharge conduit thereby allowing the gas in the secondary waste vessel to be drawn through the discharge conduit into the primary waste vessel and out of the primary waste vessel through the fill cannula. Alternatively, the present invention also contemplates that the primary and secondary vessels are evacuated prior to drug dispensement.

Method 500 desirably controls the operation of the evacuation pump as well as the operation of the pump valve and waste valve using a single synthesis device used in the production run for producing a radiopharmaceutical. The present invention contemplates that the valve between the waste vessels could be controlled by the use of programmable outputs on the synthesis device. This control would allow the emptying of the primary waste bottle to be performed automatically. Additionally, by fluidically isolating the secondary waste vessel from the primary waste vessel during the synthesis run, it may be possible under GMP to incorporate the method of the present invention retrospectively in validated process through ordinary change control processes.

The method of the present invention may alternatively be described as performing the following steps:

1) Opening the waste valve along a conduit extending between primary and secondary waste containers;

2) Pumping down both waste containers to a low pressure, desirably about −800 mbar, by drawing from the secondary waste container and out through the primary waste container;

3) Closing the waste valve;

4) Directing waste fluid into the primary waste vessel;

5) Opening the waste valve and optionally pumping nitrogen into the primary waste vessel;

6) Transferring waste liquid from the primary waste vessel to the secondary waste vessel by force of the pressure differential between the primary waste vessel and the secondary waste vessel.

The present invention contemplates that the waste vessels may be evacuated, or pumped down, to the low pressure at any stage in the synthesis sequence since any gas that comes from the secondary waste vessel will bubble through any solution in the primary waste vessel and to the vacuum pump. As described herein, it may be desirable to perform the evacuation, or pumping down, step after waste fluid has been delivered to the primary waste vessel during a synthesis run so that the drug product may be dispensed prior to transferring the waste fluid from the primary waste vessel to the secondary waste vessel.

It will also be appreciated, with additional reference to FIG. 1, that the present invention provides a method 600 for preparing a secondary waste vessel to receive a waste fluid that includes steps 502, 504, 506, and 508.

Figure 2:
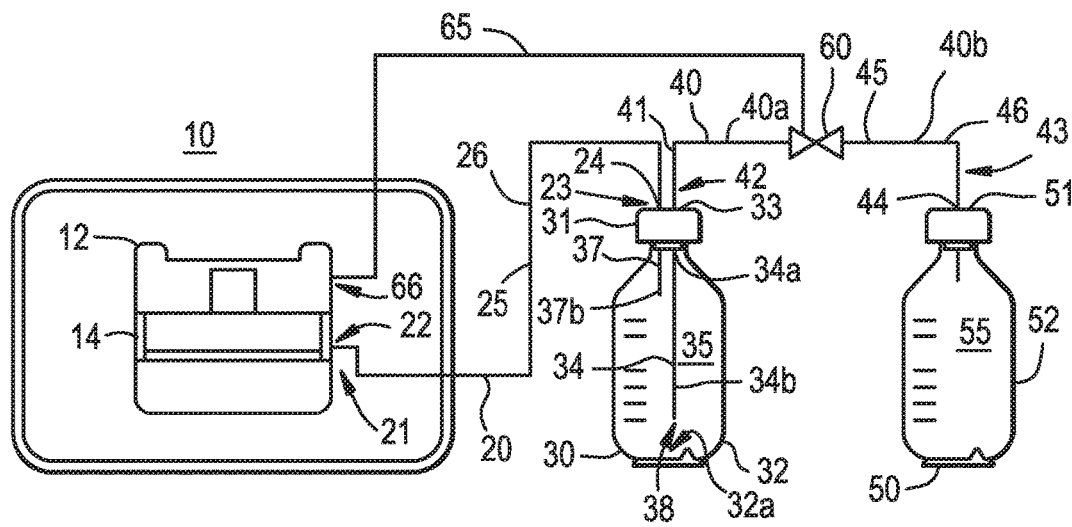
FIG. 2 depicts a system of the present invention.

With reference to FIG. 2, the present invention provides a system 10 for synthesizing a radiopharmaceutical which can direct fluid from a primary waste vessel serially connected to a secondary waste vessel serially through a waste valve by drawing a low pressure in the secondary waste vessel through the primary waste vessel and then closing the waste valve so as to fluidically isolate the secondary waste vessel from the primary waste vessel. System 10 includes an automated synthesis device 12 having a disposable cassette 14 attachable thereto. Cassette 14 includes a manifold having valves and pumps and reagent vials. Opposing ends of the cassette manifold connect to vacuum ports of synthesis device 12. Cassette 14 desirably includes at least one reaction vessel connected along the manifold which is received in a heating well on synthesis device 12. Synthesis device 12 desirably includes a vacuum pump and provides for connecting the reagent vials to the cassette manifold as well as for operation of the valves and pumps on cassette 14. Synthesis device 12 also desirably includes a source of inert gas for use in pressuring the primary waste vessel according to the method of the present invention. Cassette 14 provides for connection to a source of a radioisotope as well as a source of sterile water. Conduits from the cassette manifold lead to one or more dispense vessels, allowing for a dose as well as a quality-control (QC) volume to be dispensed to individual vessels. Additionally, a first fluid conduit 20 extends from the manifold of cassette 14 to a primary waste vessel 30. A second fluid conduit 40 extends from primary waste vessel 30 to a secondary waste vessel 50. A waste valve 60 is positioned along secondary fluid conduit 40 which is may be actuated so as to allow or prevent fluid flow from primary waste vessel 30 to secondary waste vessel 50.

The present invention contemplates that synthesis device 12 may be a FASTlab® automated synthesizer sold by GE Healthcare of Liege, Belgium. Cassette 14 includes a 3-way manifold valve having an outlet port connectable to first fluid conduit 20. When cassette 14 is attached to synthesis device 12, this manifold valve, herein referred to as the pump valve, is interposed between the pumps of both synthesis device 12 and cassette 14 and the primary waste vessel 30. Synthesis device 12 desirably includes a control system which provides for automated operation of synthesis device 12, including cassette 14, in order to produce a radiopharmaceutical. Desirably, synthesis device 12 is programmed to recognize the type of radiopharmaceutical to be synthesized on a particular cassette 14 and selects the appropriate synthesis protocol for operating cassette 14. Additionally, synthesis device 12 desirably further includes a programmable electrical output connected to an electromechanical or pneumatic waste valve 60 so as to govern its opening and closing in accordance with the present invention. For example, waste valve 60 could be controlled in the FASTlab sequence by a connection 65 to one of the available 24V programmable outputs 66 on the synthesis device 12 so that the emptying of the primary waste bottle may be performed automatically by the synthesis device 12 after a first production run.

The present invention further contemplates that the system of the present invention includes an evacuation pump and pump valve in serial connection to the primary waste vessel 30 in serial connection to a secondary waste vessel 50. While the evacuation pump and pump valve are desirably provided as part of synthesis device 12 and cassette 14, the present invention further contemplates that the evacuation pump and pump valve may be provided separately from a synthesis device. In such embodiments, the pump valve is positioned between the evacuation pump and the primary waste vessel. It is contemplated that in these alternate embodiments, the pump valve may be a 3-way valve provides the primary waste vessel in selectable communication with either evacuation pump or a source of a waste fluid.

First fluid conduit 20 includes first end 21, a second end 23 and an elongate hollow conduit body 25 extending therebetween. Conduit body 25 thus defines a first open end 22 at first end 21, a second open end 24 at second end 23, and an elongate fluid passageway 26 extending in open fluid communication therebetween. First end 21 is connected to an outlet port of the pump valve while second end 23 is connected to an inlet port 31 of primary waste vessel 30. Conduit body 25 is desirably formed from a flexible elastomeric material suitable for conducting radioactive fluids.

Primary waste vessel 30 includes a generally cylindrical body 32 defining inlet port 31, an outlet port 33 and a primary waste vessel cavity 35 in fluid communication with ports 31 and 35. Vessel cavity 35 is contemplated to have a volume sufficient to hold the waste fluid produced by at least one production run by synthesis device 12 and cassette 14. For example, certain FASTlab synthesis runs expel about 110 ml of reagents although in some processes additional bulk reagents or fluids may be used which could generate over 130 ml in total waste fluid. A typical waste vessel will hold a volume of about 250 ml. As it may not be practical to simply increase the size of the waste vessel due to limitations of space available within a hot cell, the present invention allows for multiple production runs even when the production run fills more than half of the available volume in the waste vessel.

Primary waste vessel 30 may further include an elongate open evacuation cannula 34 depending from outlet port 33. Cannula 34 includes a tubular body 36 defining an elongate open cannula passageway 38 therethrough. A proximal end 34a of cannula 34 is affixed to vessel body 32 adjacent to outlet port 33 while an opposed distal end 34b of cannula 34 extends deep into cavity 35. The present invention contemplates that distal end 34b of cannula 34 may extend all the way to, or substantially adjacent to, the floor 32a of waste vessel 30 as a minimum offset of passageway 38 from floor 32a is achieved. Floor 32a is desirably the lowest surface within cavity 35 so that evacuation cannula 34 is able to maximize the emptying of a waste fluid from cavity 35 to secondary waste vessel 50.

FIG. 2 also depicts an optional elongate open fill cannula 37 depending from inlet port 31 into cavity 34. The present invention contemplates that fill cannula 37 is not necessary for the present invention but that its illustration in FIG. 2 illustrates how the free end of 34b of evacuation cannula 34 desirably extends deeper into cavity 34 than the free end 37b of fill cannula 37 so as to enable more complete evacuation of a waste fluid from primary waste vessel 30 into secondary waste vessel 50.

Second fluid conduit 40 includes first end 41, a second end 43 and an elongate hollow conduit body 45 extending therebetween. Conduit body 45 thus defines a first open end 42 at first end 41, a second open end 44 at second end 43, and an elongate fluid passageway 46 extending in open fluid communication therebetween. First end 41 is connected to outlet port 33 of primary vessel 30 while second end 43 is connected to an inlet port 51 of secondary waste vessel 50. Conduit body 45 is desirably formed from a flexible elastomeric material suitable for conducting radioactive fluids.

Secondary waste vessel 50 includes a generally cylindrical body 52 defining inlet port 51 and a primary vessel cavity 55 in fluid communication with port 51. Vessel cavity 55 is contemplated to have a volume sufficient to hold the waste fluid produced by at least one production run by synthesis device 12 and cassette 14. For example, vessel cavity may have a volume of about 250 ml. Furthermore, it is contemplated that secondary waste vessel 50 may be placed outside of the hot cell in a location that is desirably also shielded so as to protect any operators from radiation exposure risks from the waste fluid. Desirably, secondary waste vessel 50 is significantly larger in volume than primary waste vessel 30 so that it can accept multiple discharges from primary waste vessel 30 and thus give an operator ample opportunity to allow the radioactivity in the waste fluid to decay before secondary waste vessel 50 must be emptied. The present invention further contemplates that secondary waste vessel 50 supports a secondary fill cannula 56, which descends from port 51 to a free end 56a, so further assist in directing a waste fluid into cavity 55. Desirably, secondary fill cannula 56 only descends a short distance into cavity 55 so as to allow for maximum gas evacuation from cavity 55 in accordance with the present invention. That is, by minimizing the distance that fill cannula 56 extends into cavity 55 the present invention may minimizing the risk of back syphoning from secondary waste vessel 50 while drawing low pressure therein while it contains fluid from a previous synthesis run. It will be appreciated that using port 51 without a secondary fill cannula 56, as port 51 is in fluid communication with cavity 55, would maximize the capacity of vessel 50 to accept a waste fluid discharge.

Waste valve 60 is desirably an electromechanical valve that is remotely operated, desirably by the synthesis device 12. The present invention contemplates that waste valve 60 may be a pinch valve which acts upon the outer surface of second fluid conduit 40 so as to collapse a portion of fluid passageway 46 extending through the pinch valve. Where waste valve 60 is a pinch valve, it may be desirable to employ a valve that is biased to the closed configuration, although it is further contemplated that waste valve 60 may be biased to an open configuration so as not to over-stress the fluid conduits with prolonged closure prior to its (the valve) being opened. Alternatively, the present invention contemplates that waste valve 60 may be a 2-way solenoid valve having an inlet port, an outlet port, and a waste valve passageway in interruptible fluid communication therebetween. In this alternate embodiment, second fluid conduit may be considered to be cut into a first segment 40a extending between outlet port 33 of primary waste vessel 30 and the inlet port of waste valve 60 and second segment 40b extending between the outlet port of waste valve 60 and inlet port 51 of secondary waste vessel 50 and solenoid valve 60 is desirably biased to the closed position.

In any embodiment, it is contemplated that waste valve 60 is operable to be configured in either a first configuration which fluidically isolates cavity 55 of secondary waste vessel from cavity 35 of primary waste vessel 30 or in a second configuration which places cavity 55 in fluid communication with cavity 35. In the second configuration valve 60 will allow for cavity 55 to first be evacuated to a low pressure and then to cause waste fluid to flow from cavity 35 to cavity 55 while in the first configuration valve 60 will maintain the low pressure in cavity 55 while waste fluid is directed into cavity 35.

Figure 3:
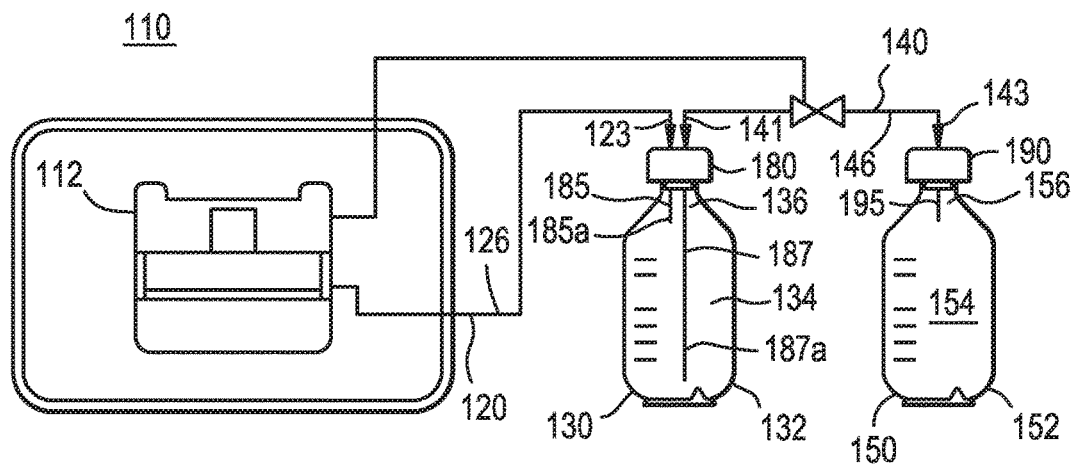
FIG. 3 depicts an alternate system of the present invention.

In an alternate embodiment of the present invention, a system 110 is depicted in FIG. 3 having primary waste vessel 130 having a vial body 132 defining a vial cavity 134 and an open vial mouth 136 in fluid communication therewith. In such an embodiment, primary waste vessel 130 includes an elastomeric septum 180 spanning mouth 136 so as to fluidically isolate cavity 134 from its surrounding environment. First fluid conduit 120 may thus support an elongate rigid hollow needle 185 at second end 123 for insertion transiting through septum 180 so as to place cavity 134 in fluid communication with first conduit passageway 126. Similarly, second fluid conduit 140 may similarly support an elongate rigid hollow needle 187 at first end 141 thereof for insertion transiting through septum 180 so as to likewise place fluid cavity 134 in fluid communication with second conduit passageway 146. It is desirable that the free end 187a of needle 147 extend further into cavity 134 than the free end 185a of needle 185. As further shown in FIG. 3, secondary waste vessel 150 includes a vial body 152 defining a vial cavity 154 and an open vial mouth 156 in fluid communication therewith. In such an embodiment, secondary waste vessel 150 may include an elastomeric septum 190 spanning mouth 136 so as to fluidically isolate cavity 134 from its surrounding environment. Second fluid conduit 140 may thus support an elongate rigid hollow needle 195 at second end 143 for insertion transiting through septum 190 so as to place cavity 154 in fluid communication with second fluid conduit passageway 146.

Figure 4:
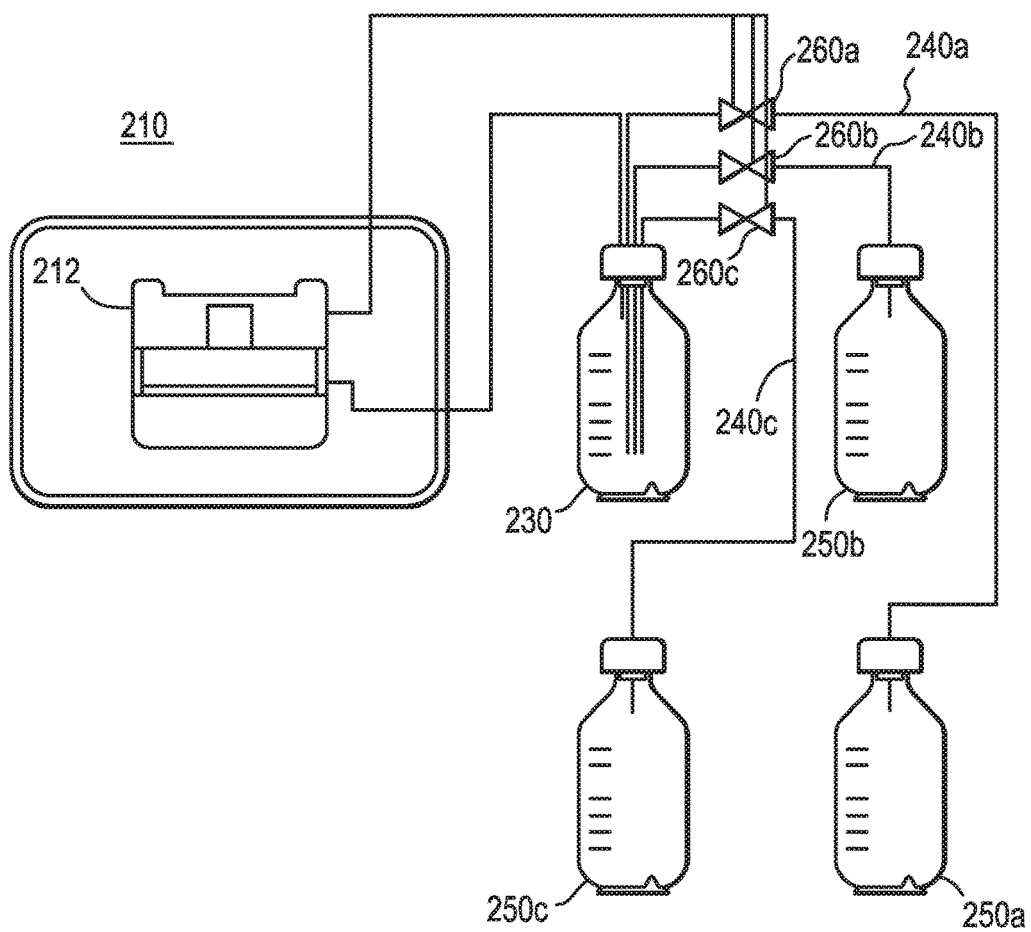
FIG. 4 depicts another system of the present invention.

The present invention further contemplates, as shown in FIG. 4, a dispense system 210 having multiple secondary waste vessels 250a-c connected in parallel to the primary waste vessel 230 such that each fluid conduit extending to a secondary waste vessel includes a waste valve 250a-c therealong. In such multiple secondary waste vessel embodiments, each secondary waste vessel 250a-c may have a low pressure drawn and maintained therein so that by opening only one of the available waste valves the contents of the primary waste vessel may be evacuated into the associated secondary waste vessel. Desirably, each of valves 260a-c is individually controlled by an individual programmable outlet on synthesis device 212. Alternatively, each of second fluid conduits 240a-c could have their first ends connect to a multi-port valve positioned between waste valves 260a-c and a primary waste conduit segment spanning between the multi-port valve and an outlet port of primary waste vessel 230.

Experimental Set-Up and Results

The dispense port of a FASTlab synthesizer was connected to a primary waste bottle through ¼" OD silicone tubing (8 meters) to a secondary waste vessel as shown in FIG. 1. Both waste vessels were at the same height. A two-way normally closed solenoid pinch valve; 24 VDC, ⅛" ID×¼" OD tubing (Cole Palmer ID WZ-98302-16), controlled from the FASTlab synthesizer, was used to isolate the secondary vessel. The primary waste vessel was filled with 150 ml of water. Then a FASTlab synthesis sequence was executed to evacuate both waste vessels down to −800 mbar with the valve in the open position. A positive pressure differential of +1000 mbar was then applied to the primary vessel and the fluid was observed to transfer from the primary waste vessel to the secondary in around 30 seconds.

While the particular embodiment of the present invention has been shown and described, it will be apparent to those skilled in the art that changes and modifications may be made without departing from the teachings of the invention. The matter set forth in the foregoing description and accompanying drawings is offered by way of illustration only and not as a limitation. The actual scope of the invention is intended to be defined in the following claims when viewed in their proper perspective based on the prior art.

What is claimed is:

1. A method for directing a waste fluid from a radiopharmaceutical synthesis system to a waste vessel comprising:
    serially connecting a primary waste vessel to a secondary waste vessel with a fluid conduit, including a waste valve connected to said fluid conduit extending between the primary waste vessel and secondary waste vessel, wherein the primary waste vessel includes a discharge conduit extending substantially to a lowest surface within the primary waste vessel such that the discharge conduit is connected to the fluid conduit;
    opening the waste valve so as to allow fluid communication between cavities of the primary and secondary waste vessels;
    drawing a low pressure in both waste vessels;
    closing the waste valve so as to fluidically isolate the secondary waste vessel from the primary waste vessel;
    discharging the waste fluid through a pump valve into the primary waste vessel, and
    opening the waste valve so that the low pressure in the secondary waste vessel evacuates the waste fluid from the primary waste vessel into the secondary waste vessel.

2. The method of claim 1, wherein the discharge conduit includes a free end positioned substantially adjacent to the floor of a cavity defined by the primary waste vessel.

3. The method of claim 2, further comprising the step of discharging the waste fluid into the cavity of the primary waste vessel to a level which submerges the free end of the discharge conduit.

4. The method of claim 3, the step of discharging the waste fluid is performed prior to the drawing step.

5. The method of claim 1, wherein the method further comprises the step of applying pressure to the waste fluid in the primary waste vessel.

6. The method of claim 1, wherein said drawing step further comprises the step of connecting an evacuation pump through a pump valve to said primary waste vessel such that gas within said secondary waste vessel is drawn through said primary waste vessel.

7. The method of claim 6, wherein drawing step further comprises drawing the pressure within said secondary waste vessel to about 900 mbar.

8. The method of claim 6, wherein said drawing step further comprises the step of switching the pump valve to an open position in order to provide pressure to said primary waste vessel.

9. The method of claim 1, wherein a synthesis device which produces the waste fluid performs said drawing step and further controls the operation of said waste valve.

10. The method of claim 1, wherein said discharging step further comprises the step of discharging the waste fluid from an automated synthesizer device.

11. A method for preparing a waste vessel to receive a waste fluid from a radiopharmaceutical synthesis system, said method comprising the steps of:
    serially connecting a primary waste vessel to a secondary waste vessel with a fluid conduit, including a waste valve connected to the fluid conduit extending between the primary waste vessel and secondary waste vessel;
    opening the waste valve so as to allow fluid communication between the cavities of the primary and secondary waste vessels;
    drawing a low pressure in both waste vessels;
    closing the waste valve so as to fluidically isolate the secondary waste vessel from the primary waste vessel.

12. The method of claim 11, wherein the primary waste vessel includes a discharge conduit extending substantially to a lowest surface within the primary waste vessel.

13. The method of claim 12, wherein the discharge conduit includes a free end positioned substantially adjacent to the floor of a cavity defined by the primary waste vessel.

14. The method of claim 11, wherein said drawing step further comprises the step of connecting an evacuation pump through a pump valve to said primary waste vessel such that gas within said secondary waste vessel is drawn through said primary waste vessel.

15. The method of claim 11, wherein drawing step further comprises drawing the pressure within said secondary waste vessel to about 900 mbar.

16. The method of claim 11, wherein an automated synthesizer device performs said drawing step and further controls the operation of said waste valve.

* * * * *